(12) United States Patent
Lee

(10) Patent No.: US 10,014,744 B2
(45) Date of Patent: Jul. 3, 2018

(54) DIRECT COOLING TYPE HANDPIECE

(71) Applicant: MICRO-NX Co., Ltd, Gyeongsangbuk-do (KR)

(72) Inventor: Jong Kun Lee, Daegu (KR)

(73) Assignee: MICRO-NX Co., Ltd, Gyeongsangbuk-do (KR)

( * ) Notice: Subject to any disclaimer, the term of this patent is extended or adjusted under 35 U.S.C. 154(b) by 234 days.

(21) Appl. No.: 15/089,587

(22) Filed: Apr. 4, 2016

(65) Prior Publication Data
US 2017/0288492 A1    Oct. 5, 2017

(51) Int. Cl.
| | |
|---|---|
| *A61C 1/16* | (2006.01) |
| *H02K 5/20* | (2006.01) |
| *H02K 7/08* | (2006.01) |
| *H02K 11/33* | (2016.01) |
| *H02K 11/00* | (2016.01) |
| *A61C 1/00* | (2006.01) |
| *A61C 1/08* | (2006.01) |
| *A61C 1/06* | (2006.01) |

(52) U.S. Cl.
CPC ............ *H02K 5/20* (2013.01); *A61C 1/0069* (2013.01); *A61C 1/06* (2013.01); *A61C 1/088* (2013.01); *A61C 1/16* (2013.01); *H02K 7/085* (2013.01); *H02K 11/0094* (2013.01); *H02K 11/33* (2016.01)

(58) Field of Classification Search
CPC ........... A61C 1/06; A61C 1/0069; A61C 1/18; A61C 1/02
USPC ............................................ 310/50; 433/131
See application file for complete search history.

(56) References Cited

U.S. PATENT DOCUMENTS

| | | | | |
|---|---|---|---|---|
| 7,267,547 | B2 * | 9/2007 | Schmid ................ | A61C 1/0069 433/32 |
| 2003/0165794 | A1 * | 9/2003 | Matoba ................ | A61C 1/0007 433/114 |
| 2011/0027752 | A1 * | 2/2011 | Pollock ................... | A61C 1/18 433/119 |
| 2013/0342050 | A1 * | 12/2013 | Duesing .................. | H02K 5/08 310/59 |

* cited by examiner

*Primary Examiner* — Terrance Kenerly
(74) *Attorney, Agent, or Firm* — Hauptman Ham, LLP

(57) ABSTRACT

The present invention relates to a direct cooling type handpiece, and more particularly, to a direct cooling type handpiece that is configured to allow an outer housing and a core to be spaced apart from each other and thus to allow the core to be fixed to a PCB and a support cap, so that air flows to the space between the outer housing and the core, thus efficiently cooling the high heat generated from the handpiece while the handpiece is being operated.

4 Claims, 2 Drawing Sheets

DIRECT COOLING TYPE HANDPIECE

BACKGROUND OF THE INVENTION

Field of the Invention

The present invention relates to a direct cooling type handpiece, and more particularly, to a direct cooling type handpiece that is configured to allow an outer housing and a core to be spaced apart from each other and thus to allow the core to be fixed to a PCB and a support cap, so that air flows to the space between the outer housing and the core, thus efficiently cooling the high heat generated from the handpiece while the handpiece is being operated.

Background of the Related Art

Generally, handpieces are used for the purpose of dental laboratory when teeth are cut or polished in a dental clinic, for the purpose of nail art when nails are trimmed in a nail shop, and for the purpose of machining when jewelry is machined.

At this time, the handpiece has a high speed motor operating at 40,000 rpm with the power received thereto, and during the operation of the high speed motor, accordingly, excessive heat may be absolutely generated from the handpiece.

So as to cool the heat generated from the handpiece due to the operation of the high speed motor, conventionally, saline solution, electric current, or air is applied to the handpiece.

In case of the conventional saline solution application, however, a pipe for supplying the saline solution is located on the outside of a core, and accordingly, the pipe just cools the heat generated from the high speed motor in an indirect manner, thus exhibiting weak cooling effects. Further, the saline solution should be continuously applied to the pipe. In case of the conventional electric current application, on the other hand, the handpiece is complicated in configuration, and the heat generated from the high speed motor is not efficiently cooled.

In case of the conventional air application, further, air does not flow gently so that it just cools the space around an impeller, thus failing to totally cool the interior of the handpiece and the high speed motor.

Accordingly, the heat generated upon the operation of the high speed motor of the conventional handpiece is not efficiently cooled, thus undesirably causing vibrations and noise to be generated upon the operation of the high speed motor.

So as to solve the above-mentioned problems, accordingly, there is proposed Korean Patent No. 10-1461992 as issued to the same applicant as the present invention, which discloses a handpiece having a direct cooling type slimmed driving part, and the conventional handpiece is configured to pass air and water through a core to cool high heat generated therefrom. Therefore, the present invention is an improvement of the handpiece disclosed in Korean Patent No. 10-1461992 as issued to the same applicant as the present invention.

SUMMARY OF THE INVENTION

Accordingly, the present invention has been made in view of the above-mentioned problems occurring in the prior art, and it is an object of the present invention to provide a direct cooling type handpiece that is configured to allow an outer housing and a core to be spaced apart from each other and thus to allow the core to be fixed to a PCB and a support cap, so that air flows to the space between the outer housing and the core, thus efficiently cooling the high heat generated from the handpiece while the handpiece is being operated.

To accomplish the above-mentioned object, according to the present invention, there is provided a direct cooling type handpiece including: an outer housing provided in a rod shape in such a manner as to be graspable by a user's hand; a cylindrical core inserted into the inner peripheral surface of the outer housing in such a manner as to be spaced apart from the outer housing and having a coil wound along the inner peripheral surface thereof and cooling holes penetrated into the outer peripheral surface thereof; cylindrical cooling pipes inserted into the cooling holes formed on the core to allow water and air to flow therealong; a cylindrical flowing pipe adapted to flow air to one side of the space between the outer housing and the core; a rotor inserted into the core, provided with transmission shafts extended forwardly and backwardly from both sides thereof, and made of a cylindrical magnetic body; a cylindrical PCB disposed on one side of the core in such a manner as to be fitted to one side transmission shaft of the rotor to transmit electric current to the core and the rotor and further coming into contact with the core in such a manner as to support the core thereagainst, while passing the cooling pipes and the flowing pipe therethrough; a pair of bearings fitted to the transmission shafts in such a manner as to allow the rotor to be rotatably supported thereagainst; a coupling disposed on the front side of the rotor in such a manner as to be coupled to the other side transmission shaft; a front housing coupled to the front side of the outer housing and having water and air discharging holes formed on the outer peripheral surface thereof to discharge the water and air supplied from the cooling pipes therefrom, while being penetrated from the front side thereof to the rear side thereof to insert the other side transmission shaft and the coupling thereinto; a support cap disposed on the other side of the core contacted with the PCB in such a manner as to accommodate one side bearing in the intermediate portion thereof and having a protruding outer periphery adapted to support one side of the core and through holes formed to insert the front ends of the cooling pipes thereinto; a front cap disposed on one side of the PCB to fix the cooling pipes and the flowing pipe thereto; a rear cap disposed on one side of the front cap and having a power term located on one side thereof to supply the electric current to the PCB; and a rear housing coupled to the rear side of the outer housing so as to relay the supply of the electric current, air and water from the outside.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENTS

Hereinafter, an explanation on a direct cooling type handpiece according to the present invention will be in detail given with reference to the attached drawings.

Figure 1:
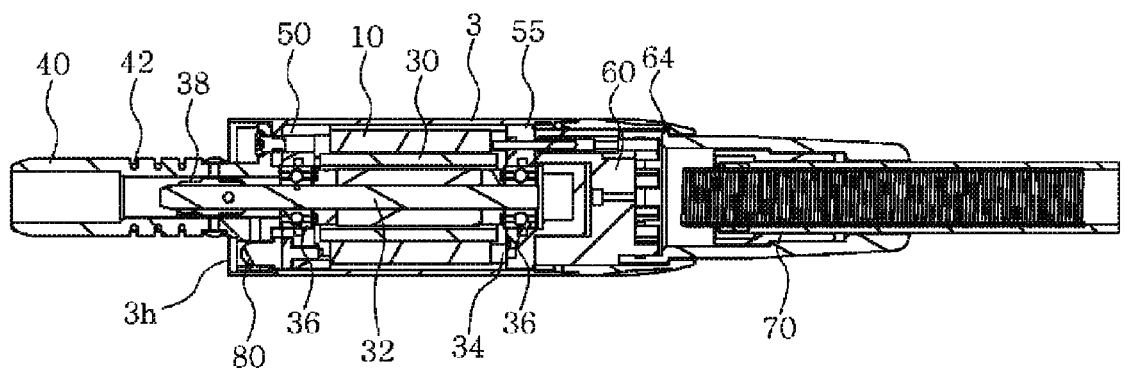
FIG. 1 is a sectional view showing a direct cooling type handpiece according to the present invention.
Figure 2:
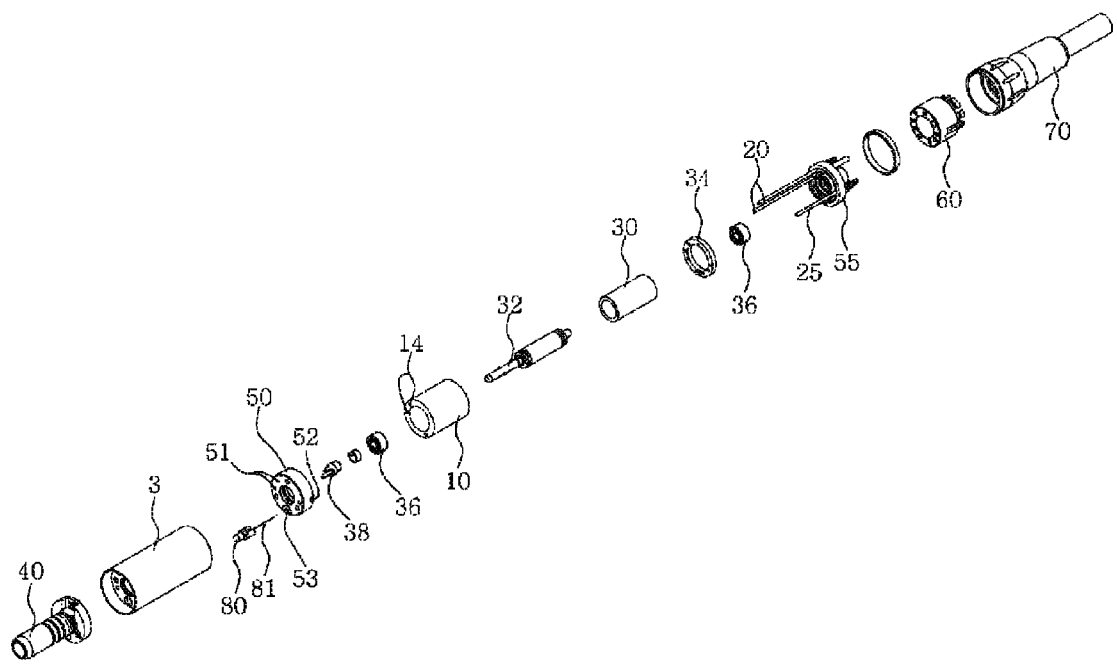
FIG. 2 is an exploded perspective view showing the direct cooling type handpiece according to the present invention.

Referring to FIGS. 1 and 2, a direct cooling type handpiece according to the present invention has an outer housing 3 provided in a shape of a rod open on the front and rear sides thereof in such a manner as to be graspable by a user's hand.

The diameter of the intermediate periphery of the outer housing 3 is smaller than the diameters of the front and rear peripheries thereof, and the outer housing 3 has a plurality of protrusions formed on the outer peripheral surface of the rear side thereof so that it can be stably grasped by the user's hand.

According to the present invention, further, the direct cooling type handpiece includes a cylindrical core 10 inserted into the inner peripheral surface of the outer housing 3 in such a manner as to be spaced apart from the outer housing 3 and having a coil wound along the inner peripheral surface thereof, the coil being adapted to rotate a rotor 30 as will be discussed later, and cooling holes 14 formed penetratedly formed from the front side thereof to the rear side thereof on the outer peripheral surface thereof in such a manner as to insert cooling pipes 20 as will be discussed later thereinto.

Accordingly, air is supplied to the space between the core 10 and the inner peripheral surface of the outer housing 3 through a cylindrical flowing pipe 25.

The cooling pipes 20 are cylindrical pipes inserted into the cooling holes 14 formed on the core 10 to allow water and air to flow therealong, and the flowing pipe 25 is a cylindrical pipe flowing air to one side of the space between the outer housing 3 and the core 10.

That is, the cooling pipes 20 supply the water and air used for the operation of the handpiece to the front end periphery of the outer housing 3, and the flowing pipe 25 flows the air to the space between the outer housing 3 and the core 10, so that the cool air generated from the air and water is sent to the core 10, thus cooling the high heat generated upon the operations of the core 10 and the rotor 30.

According to the present invention, furthermore, the direct cooling type handpiece includes the rotor 30 inserted into the core 10, provided with transmission shafts 32 extended forwardly and backwardly from both sides thereof, and made of a cylindrical magnetic body.

The rotor 30 is inserted into the inner peripheral surface of the core 10 in such a manner as to be spaced apart therefrom and desirably operated at 40,000 rpm with the power supplied thereto. If the rotor 30 and the core 10 are operated at 40,000 rpm or under, the handpiece cannot perform tooth cutting gently when used in a dental clinic, and contrarily, if the rotor 30 and the core 10 are operated at 40,000 rpm or more, excessive heat is generated from the rotor 30 and the core 10, so that they may be damaged or broken out.

According to the present invention, further, the direct cooling type handpiece includes a cylindrical PCB 34 disposed on one side of the core 10 in such a manner as to be fitted to one side transmission shaft 32 of the rotor 30 to transmit electric current to the core 10 and the rotor 30 and further coming into contact with the core 10 in such a manner as to support the core 10, while passing the cooling pipes 20 and the flowing pipe 25 therethrough.

The PCB 34 serves to transmit the electric current to the core 10 and the rotor 30 as well as to a wiring portion 81 of an LED 80 as will be discussed later.

Also, the direct cooling type handpiece includes a pair of bearings 36 fitted to the transmission shafts 32 in such a manner as to allow the rotor 30 to be rotatably supported thereagainst.

According to the present invention, further, the direct cooling type handpiece includes a coupling 38 disposed on the front side of the rotor 30 in such a manner as to be coupled to the other side transmission shaft 32, and even if not shown in the drawings, a shaft and a worm gear are connected sequentially to the front side of the coupling 38 to rotate a drill of the handpiece.

According to the present invention, moreover, the direct cooling type handpiece includes a front housing 40 coupled to the front side of the outer housing 3 and having water and air discharging holes 42 formed on the outer peripheral surface thereof to discharge the water and air supplied from the cooling pipes 20 therefrom, while being penetrated from the front side thereof to the rear side thereof to insert the other side transmission shaft 32 and the coupling 38 thereinto.

At this time, the water and air discharging holes 42 are formed on the front housing 40, and of course, the number of water and air discharging holes 42 may be increased in accordance with the number of the cooling pipes 20.

According to the present invention, moreover, the direct cooling type handpiece includes a support cap 50 disposed on the other side of the core 10 contacted with the PCB 34 in such a manner as to locate the other side bearing 36 on the center thereof, the other side bearing 36 being disposed on the other side of the core 10 to rotatably support the transmission shaft 32 thereagainst, and having a protruding' outer periphery adapted to support one side of the core 10, through holes 51 formed to insert the front ends of the cooling pipes 20 thereinto, and a guide groove 52 formed to flow the air supplied from the space between the outer housing 3 and the core 10 to the opposite side thereto.

According to the present invention, further, the direct cooling type handpiece includes a front cap 55 disposed on one side of the PCB 34 to fix the cooling pipes 20 and the flowing pipe 25 thereto and a rear cap 60 disposed on one side of the front cap 55 and having a power terminal 64 located on one side thereof to supply the electric current to the PCB 34.

According to the present invention, furthermore, the direct cooling type handpiece includes a rear housing 70 coupled to the rear side of the outer housing 3 so as to relay the supply of the electric current, air and water from the outside, and even if not shown in the drawings, the rear housing 70 is used by connecting connectors having power and supply hoses thereto. At this time, conventional connectors as the connectors may be used, and otherwise, other types of connectors may be used.

According to the present invention, the direct cooling type handpiece is configured wherein the water and air pass through the cooling holes 14 of the core 10 and at the same time the air supplied from the flowing pipe 25 flows to the space between the outer housing 3 and the core 10, so that the high heat generated upon the operation of the handpiece is efficiently cooled, thus preventing the life span of the handpiece from being reduced due to the overheating and further avoiding the generation of vibrations and noise from the handpiece.

On the other hand, the support cap 50 further has a seating groove 53 formed on the front side thereof to seat the LED 80 and the wiring portion 81 receiving the electric current from the LED 80 thereonto. Further, the wiring portion 81 is extended to the rear housing 70 in such a manner as to receive the electric current therefrom.

Moreover, the wiring portion 81 is resistant to water.

Also, the outer housing 3 has a through hole 3h formed penetratedly from the front side to the rear side on one side thereof at which the LED 80 is located so as to irradiate the light generated from the LED 80 to the outside.

That is, the light generated from the LED 80 located on the support cap 50 is irradiated to the outside through the through hole 3*h* of the outer housing 3, so that when the handpiece is used in a dental clinic or nail shop, the field of vision of the user can be sufficiently ensured, thus improving the conveniences in use.

Further, the wiring portion 81 is inserted into a protection body 56 disposed on the front cap 55, and accordingly, no additional space for supplying the electric current to the LED 80 is required, thus allowing the volume of the handpiece to be slim, so that while the handpiece is being easily grasped by the user, the wiring portion 81 is protected by means of the formation of the protection body 56, thus enabling the electric current to be stably supplied.

Furthermore, the single LED 80 is shown in the drawing, but the number of LEDs may be increased in accordance with the control of the brightness of the light.

As described above, the direct cooling type handpiece according to the present invention is configured wherein the water and air pass through the cooling holes of the core and at the same time the air supplied from the flowing pipe flows to the space between the outer housing and the core, so that the high heat generated upon the operation of the handpiece is efficiently cooled, thus preventing the life span of the handpiece from being reduced due to the overheating and further avoiding the generation of vibrations and noise from the handpiece.

Additionally, the direct cooling type handpiece according to the present invention is configured wherein the light generated from the LED located on the support cap is irradiated to the outside through the through hole of the outer housing, so that when the handpiece is used in a dental clinic or nail shop, the field of vision of the user can be sufficiently ensured, thus improving the conveniences in use.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A direct cooling type handpiece comprising:
   an outer housing 3 provided in a rod shape in such a manner as to be graspable by a user's hand;
   a cylindrical core 10 inserted into the inner peripheral surface of the outer housing 3 in such a manner as to be spaced apart from the outer housing 3 and having a coil wound along the inner peripheral surface thereof and cooling holes 14 penetrated into the outer peripheral surface thereof;
   cylindrical cooling pipes 20 inserted into the cooling holes 14 formed on the core 10 to allow water and air to flow therealong;
   a cylindrical flowing pipe 25 adapted to flow air to one side of the space between the outer housing 3 and the core 10;
   a rotor 30 inserted into the core 10, provided with transmission shafts 32 extended forwardly and backwardly from both sides thereof, and made of a cylindrical magnetic body;
   a cylindrical PCB 34 disposed on one side of the core 10 in such a manner as to be fitted to one side transmission shaft 32 of the rotor 30 to transmit electric current to the core 10 and the rotor 30 and further coming into contact with the core 10 in such a manner as to support the core 10 thereagainst, while passing the cooling pipes 20 and the flowing pipe 25 therethrough;
   a pair of bearings 36 fitted to the transmission shafts 32 in such a manner as to allow the rotor 30 to be rotatably supported thereagainst;
   a coupling 38 disposed on the front side of the rotor 30 in such a manner as to be coupled to the other side transmission shaft 32;
   a front housing 40 coupled to the front side of the outer housing 3 and having water and air discharging holes 42 formed on the outer peripheral surface thereof to discharge the water and air supplied from the cooling pipes 20 therefrom, while being penetrated from the front side thereof to the rear side thereof to insert the other side transmission shaft 32 and the coupling 38 thereinto;
   a support cap 50 disposed on the other side of the core 10 contacted with the PCB 34 in such a manner as to accommodate one side bearing 36 in the intermediate portion thereof and having a protruding outer periphery adapted to support one side of the core 10 and through holes 51 formed to insert the front ends of the cooling pipes 20 thereinto;
   a front cap 55 disposed on one side of the PCB 34 to fix the cooling pipes 20 and the flowing pipe 25 thereto;
   a rear cap 60 disposed on one side of the front cap 55 and having a power terminal 64 located on one side thereof to supply the electric current to the PCB 34; and
   a rear housing 70 coupled to the rear s de of the outer housing 3 so as to relay the supply of the electric current, air and water from the outside.

2. The direct cooling type handpiece according to claim 1, wherein the support cap 50 has a seating groove 53 formed on the front side thereof to seat the LED 80 and the wiring portion 81 receiving the electric current from the LED 80 thereinto, the wiring portion 81 being extended to the rear housing 70 in such a manner as to receive the electric current therefrom and being resistant to water.

3. The direct cooling type handpiece according to claim wherein the outer housing 3 has a through hole 3*h* formed penetratedly from the front side to the rear side on one side thereof at which the LED 80 is located so as to irradiate the light generated from the LED 80 to the outside.

4. The direct cooling type handpiece according to claim wherein the support cap 50 has a guide groove 52 formed to flow the air supplied from, the space between the outer housing 3 and the core 10 to the opposite side thereto.

* * * * *